United States Patent [19]

Mastel

[11] Patent Number: 5,201,747

[45] Date of Patent: Apr. 13, 1993

[54] OPHTHALMOLOGICAL SURGICAL INSTRUMENT HAVING A TRIPLE EDGE TIP

[76] Inventor: Douglas Mastel, 2843 Sanco Rd., Suite V, Rapid City, S. Dak. 57702-9368

[21] Appl. No.: 837,969

[22] Filed: Feb. 20, 1992

[51] Int. Cl.[5] .............................................. A61B 17/32
[52] U.S. Cl. .................................... 606/167; 606/166; 30/353
[58] Field of Search ........................ 606/107, 166, 167; 30/353, 357

[56] References Cited

U.S. PATENT DOCUMENTS

| 1,778,773 | 10/1930 | Reynolds | 30/353 |
| 2,102,930 | 12/1937 | Wharton | 30/353 |
| 4,592,113 | 6/1986 | Selfors | 30/353 |

FOREIGN PATENT DOCUMENTS 1424814  9/1988  U.S.S.R. ................................ 606/167

Primary Examiner—C. Fred Rosenbaum
Assistant Examiner—William W. Lewis
Attorney, Agent, or Firm—Frank D. Gilliam

[57] ABSTRACT

An improved surgical knife blade particularly suited to eye surgery having a triple edged truncated point. An elongated, flat diamond blade has a primal end adapted to be supported in a handle or the like and a sharp distal end adapted to penetrate and cut tissue, such as the cornea of the eye in radial keratotomy. The blade has a first edge lying generally parallel to the blade axis and a second edge at the distal blade end converging toward the first edge at a selected angle, optimally about 15°. A flat transverse tip is provided at the meeting point of the first and second edges, at an angle of from about 45° to 135° to the first blade edge. Both edges and the tip are faceted to provide uniformly very sharp edges. This blade will penetrate tissue more easily and under greater control than prior blades so that arcuate transverse incisions may be accurately made in astigmatic keratotomy. Incisions of uniform depth to nearly the ends of the incisions can be made more accurately.

13 Claims, 2 Drawing Sheets

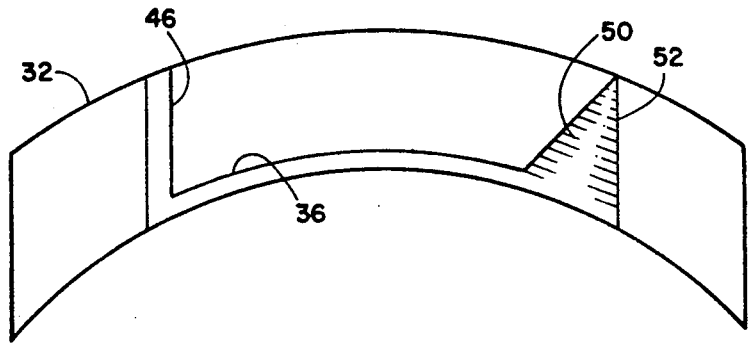
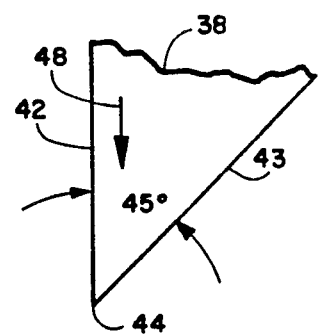
PRIOR ART
FIGURE 6
PRIOR ART
FIGURE 7
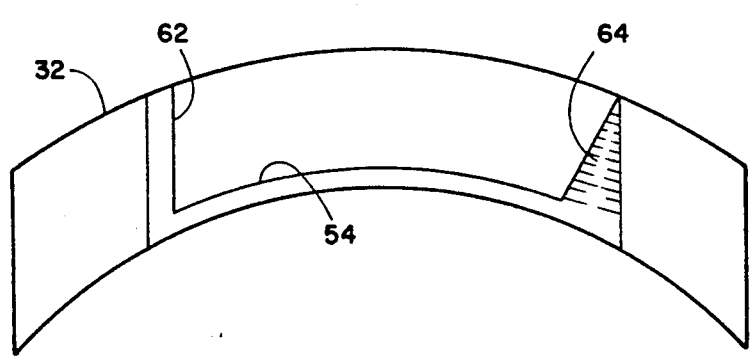
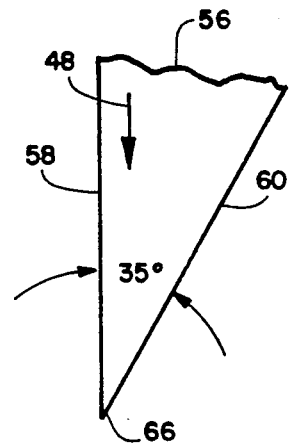
PRIOR ART
FIGURE 8
PRIOR ART
FIGURE 9
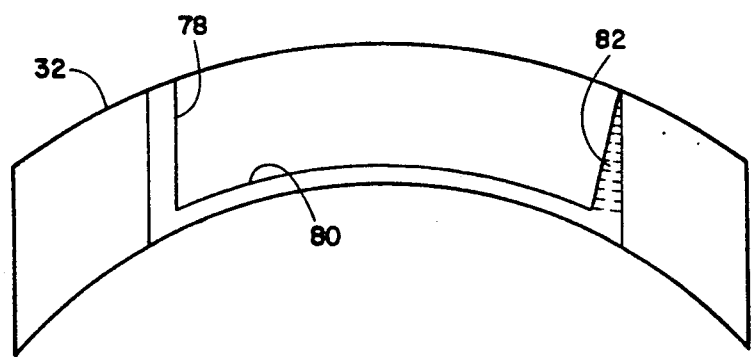
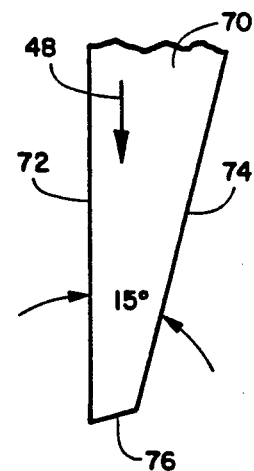
FIGURE 10
FIGURE 11

5,201,747

OPHTHALMOLOGICAL SURGICAL INSTRUMENT HAVING A TRIPLE EDGE TIP

BACKGROUND OF THE INVENTION

This invention relates in general to blades for use in surgical knives and, more specifically, to improved surgical blades for use in eye surgery, such as radial keratotomy.

A variety of different surgical blades have been developed over the years for use in different types of surgery. Conventional surgical blades have been made of steel and designed for different types of surgery, such as the blades described by Freedman in U.S. Pat. No. 4,185,634 for use in foot or hand surgery and the various surgical blade shapes described by Driest in U.S. Pat. No. 2,049,898 for use in general surgery.

As the ability to perform surgery on the eye has developed, in particular surgery of the cornea, a need for much smaller, sharper and more precise surgical blades followed. In radial keratotomy, it is often necessary to make a plurality of radial incisions in the cornea to a uniform depth. Typically, these incisions have been made using a fine knife having a pointed blade with the angle between blade edges being about 45°, as shown, for example, by Anis in U.S. Pat. No. 4,602,630. Similarly, a blade having a sharp point and an angle between blade edges of about 45° is shown by Kramer et al in U.S. Pat. No. 4,688,570 for use with a template in performing radial keratotomy. More recently, diamond blades have come into use due to their small size and ability to retain a fine, sharp edge.

While the surgical blades of the prior art are generally effective when carefully used, they suffer from a number of drawbacks. The relatively wide angle between blade edges, typically 35° to 45°, makes accurate plunging of the blade into corneal tissue to a precise depth at the start of an incision difficult. While it is generally preferred that the ends of an incision be approximately perpendicular to the surface of the eye, these blades leave sloping edges on at least one end. The pointed tips of these knives are much more fragile and susceptible to wear and damage if bumped against objects. Since these wide blades have a relatively wide blade portion in an incision, turning the blade precisely to form a number of parallel curved incisions, each with uniform radius, as is required when performing astigmatic surgery, is very difficult.

Thus, there is a continuing need for improved surgical blades for use in eye surgery and other precise surgery which permits the formation of precise incisions having ends more nearly vertical to the eye surface, allows precise formation of curved incisions and resists damage to the blade tip.

SUMMARY OF THE INVENTION

It is, therefore, an object of this invention to provide a surgical blade overcoming the above-noted problems. Another object is to provide a surgical blade in which the two blade edges converge at a shallow angle to permit easy turning of the blade in an incision so as to produce a precisely curved incision. A further object is to provide a surgical blade having a small, triple-edged, transverse tip at the blade point to resist damage and create a slope that reduces friction and permits accurate and consistent penetration into the cornea.

The above-noted objects, and others, are accomplished in accordance with this invention by an elongated, generally flat blade having one end adapted to be supported by a handle or other means of like utility and an opposite end adapted to penetrate and cut tissue. At the cutting end, one edge preferably lies substantially parallel to the length of the blade and the other edge converges toward the first edge to form an intersection. A transverse flat tip is provided between the edges just short of where the edges would otherwise intersect. The edges and tip are all shaped, such as with facets, to provide extremely sharp cutting edges on the triple-edged blade tip.

This blade, because of the shallow included angle and the transverse tip, is capable of full, accurate and consistent penetration into the cornea and can be precisely moved along a straight or curved path. This blade is ideally suited to performing "Russian" style keratotomy, "American" style keratotomy and astigmatic correction.

BRIEF DESCRIPTION OF THE DRAWING

Details of the invention, and of certain preferred embodiments thereof, will be further understood upon reference to the drawing, wherein:

FIG. 6 is a schematic section taken substantially along one of the cuts shown in FIG. 5, showing an incision made by a prior art 45° blade;

FIG. 7 is a schematic side elevation view of the prior art blade end that would make the incision shown in FIG. 6;

FIG. 8 is a schematic section taken substantially along one of the cuts shown in FIG. 5, showing an incision made by a prior art 35° blade;

FIG. 9 is a schematic side elevation view of the 35° blade that would make the incision shown in FIG. 8;

FIG. 10 is a schematic section taken substantially along one of the cuts shown in FIG. 5, showing an incision made by the blade of this invention; and FIG. 11 is a schematic side elevation view of the blade end of this invention that would make the incision shown in FIG. 6.

DETAILED DESCRIPTION OF PREFERRED EMBODIMENTS

Figures 1, 2:
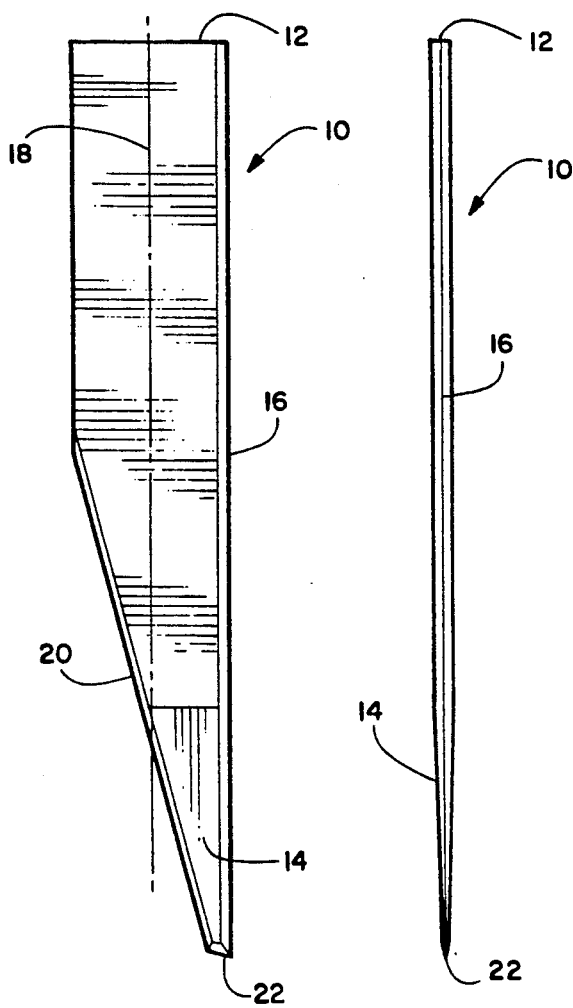
FIG. 1 is a side elevation view of the surgical blade of this invention.
FIG. 2 is a front elevation view of the surgical blade of FIG. 1.

Referring now to FIG. 1, there is seen a surgical blade 10 having a primal end 12 adapted to be secured to a conventional handle or other support means (not shown) for use. Blade 10 may be permanently fastened to a handle, or may be releasably secured to a handle to permit easy replacement of the blade, as desired. Distal end 14 includes the cutting edges. Blade 10 may have any suitable length and width. Typically, the length of blade 10 will be from about 4.5 to 6 mm, with optimum effectiveness at about 6 mm. The blade preferably has a width of from about 0.5 to 1 mm, with a width of about 1 mm generally being optimum. While the blade is ordinarily flat, with the two faces substantially parallel, other configurations may be used, if desired. Excellent results are obtained with blade thicknesses of from about 0.1 mm to 0.25 mm. A blade thickness of about 0.15 mm is optimum. Blade 10 is preferably formed from diamond in a conventional manner. Other blade materials may be used to practice this invention.

First edge 16 lies substantially parallel to the long axis 18 of the blade. Second edge 20 converges toward first edge 16 at an angle of from about 10 to 30 degrees. For best results, this angle should be about 15°. Lines along edges 16 and 18 would ordinarily meet in a point, as do the edges in prior art blades. However, a transverse tip 22 having a width of from about 0.05 to 0.30 mm is provided between edges 16 and 20, eliminating the easily damaged sharp point. Optimally, tip 22 has a width of about 0.2 mm. As mentioned above, tip 22 permits the blade to accurately plunge straight into the cornea, where a pointed blade would tend to slide off in the direction away from the sloping edge. In addition, tip 22 resists chipping or breaking both in manufacturing and clinically, which can easily occur with a fine pointed end. Tip 22 may be perpendicular to edge 16, as shown, or may slope at an angle of 45° to 135° to edge 16, as desired.

The width of the blade is preferably tapered slightly in the region of the cutting edge. Preferably, the taper is at an angle of about 2 to 5 degrees to each face, with optimum taper angles being about 6° over the last about 1.5 mm of the blade. Facets are ground along edges 16 and 20 and tip 22 to provide the required sharp edges.

Figure 3:
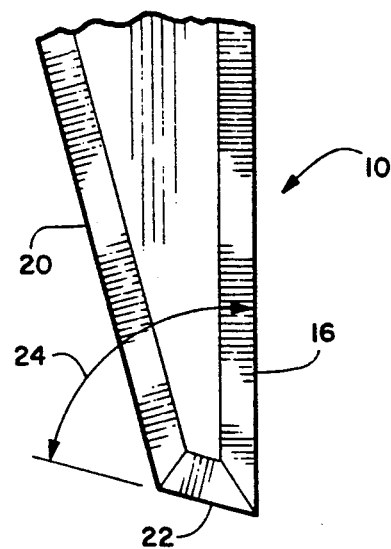
FIG. 3 is a detail side elevation view of a blade tip optimized for "American" style keratotomy.
Figure 4:
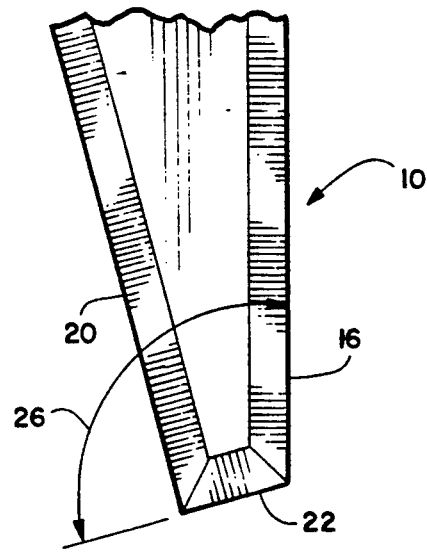
FIG. 4 is a detail side elevation view of a blade tip optimized for "Russian" style keratotomy.

As shown in detail views in FIGS. 3 and 4, blade 10 can be optimized for use in performing "American" style or "Russian" style keratotomy, respectively. In the American style, the blade is pulled toward the sloping edge 20 while in the Russian style the blade is pushed toward the straight edge 16. Preferably, tip 22 lies at an angle of from about 60° to 90° to edge 16 (as indicated by arc 24) for use in the American style and at an angle of from about 90° to 120° to edge 16 (as indicated by arc 26) for use in the Russian style. Basically, tip 22 is raised slightly in the direction of the intended blade movement.

Figure 5:
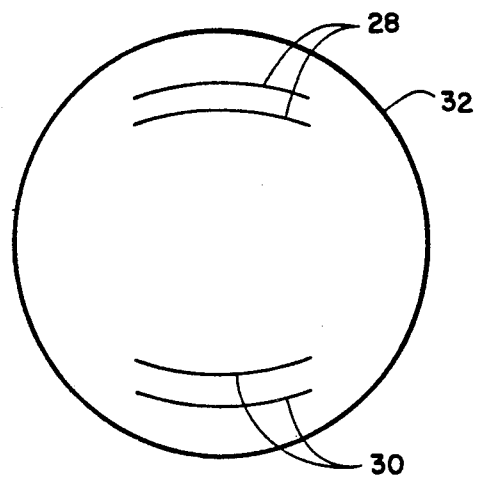
FIG. 5 is a plan view of a cornea with plural arcuate incisions.

The blade of this invention is particularly advantageous in forming arcuate transverse incisions of the type used in astigmatic keratotomy, as shown in FIG. 5. Arcuate incisions 28 and 30 are made in cornea 32 to relieve astigmatism. It is important that incisions 28 and 30 have the same radius along the entire incision. The blade of this invention permits great accuracy and uniformity in making these arcuate incisions. Of course, this blade is equally effective in forming straight incisions of the sort used in radial keratotomy.

The advantages of the blade of this invention over prior art blades is demonstrated in FIGS. 6-11. In each of FIGS. 6, 8 and 10, an arcuate incision of the sort shown in FIG. 5 is made by plunging the blade straight into the cornea 32 at one end of the desired incision, moving it to the opposite end and pulling the blade straight out of the incision. Ideally, the incision would be vertical at each end and would have very uniform depth.

The incision 36 seen in FIG. 6 is made using a conventional prior art blade 38 having a 45° end angle between edge 40 and converging edge 42, with a sharp point 44. Point 44 is easily damaged if bumped against a hard object and even for thermal cycling during autoclaving. In use, the blade 38 is plunged into the cornea 32 along vertical line 46. The intended plunge direction is indicated by arrow 48 in FIG. 7. Because the sloping edge 44 must cut into cornea 32, there is a force vector tending to slide the blade off line 46, to the left as seen in FIG. 6. Thus, the surgeon must use great care to obtain a reasonably straight plunge entry along line 46. At the end of incision 36, blade 38 is moved vertically out of the cornea, leaving an uncut area indicated by shaded area 50, well short of the desired vertical incision end line 52. Thus, the conventional 45° blade is susceptible to having the point damaged, is difficult to plunge along a straight vertical line and leaves a significant part of the desired incision uncut. The width of blade 38 in incision 36 will also make turning the blade to form a uniform and accurate arcuate incision (as seen in FIG. 5) difficult.

FIGS. 8 and 9 illustrate an incision 54 formed with blade 56 having another prior art configuration, with a 35° angle between edge 58 and converging edge 60. When blade 56 is plunged into cornea 32 along vertical line 62, vector forces against edge 60 will still tend to push the blade to the left, off of line 62, but to a lesser degree than with the blade of FIG. 7. At the completion of incision 54, the blade is withdrawn, leaving an uncut area 64. While this area 64 is smaller than with the blade of FIG. 7, it is still much larger than would be desired. The point 66 of blade 56, however, is much narrower than that of blade 38 and more susceptible to damage. Also, the width of blade 56 in incision 54 is still so great as to make turning the blade to follow an arcuate incision line (as seen in FIG. 5) difficult. Thus, simply making the angle between edge 58 and edge 60 narrower does not solve the problems of damage to the blade, which becomes increasingly severe as the blade angle becomes less, difficulty in achieving a precisely vertical plunge entry into the incision and of maintaining precise control along an arcuate incision.

The operation of the blade of this invention is illustrated in FIGS. 10 and 11. Here, blade 70 has a first edge 72 along the blade length and a converging edge 74, with a transverse tip 76 cutting off the point that would otherwise be very thin and weak. When blade 70 is plunged into cornea 32 along line 78, there is little side force to move the blade off the line, since tip 76 tends to cut straight into the cornea. Since blade 70 is relatively much narrower than prior art blades, turning the blade to follow a desired arc along incision 80 is much easier. The transverse tip 76 is much more sturdy than the prior art pointed tips and is much more resistant to damage. Finally, with the narrow 15° angle between edges 72 and 74, only a very small uncut area 82 is left at the end of an incision. The blade of this invention, thus, overcomes the problems of the prior art blades in obtaining a straight plunge incision, controlling blade movement along an arcuate incision and leaving excess uncut areas at the end of an incision. Further, this novel blade overcomes the serious problems inherent in easily damaged pointed end blades.

Other applications, variations and ramifications of this invention will occur to those skilled in the art upon reading this disclosure. Those are intended to be included within the scope of this invention, as defined in the appended claims.

I claim:

1. An ophthalmologic surgical blade which comprises:
   an elongated blade having a primal end adapted to be connected to a support means and a distal end adapted to penetrate and cut tissue;

said blade having first and second opposed cutting edges;

said first and second edges converging toward each other at an angle of from about 10 to 30 degrees;

said edges terminating at a transverse flat tip extending between said edges, said tip having a width of from about 0.05 to 0.30 mm and an angle to said first edge of from about 60° to 120°; and said edges and tip being shaped to provide sharp cutting edges.

2. The ophthalmologic surgical blade according to claim 1 wherein said angle of said flat tip to said first edge is from about 75° to 105°.

3. The ophthalmologic surgical blade according to claim 1 wherein said second edge lies at an angle to said first edge of about 15°.

4. The ophthalmologic surgical blade according to claim 1 wherein said tip has a width of approximately 0.20 mm.

5. The ophthalmologic surgical blade according to claim 1 wherein said blade thickness decreases toward said tip over a portion near said tip.

6. The ophthalmologic surgical blade according to claim 1 wherein said blade length is about 1.4 mm, width is about 1.0 mm at said primal end, and thickness is about 0.15 mm at the primal end, with the blade thickness tapering over the last 1.5 mm adjacent to said tip at an angle of about 6° to each blade surface.

7. The ophthalmologic surgical blade according to claim 1 wherein said first edge lies substantially parallel to the long axis of said blade.

8. An ophthalmologic surgical blade which comprises:

an elongated flat blade having a primal end adapted to be supported in a handle and a distal end adapted to penetrate and cut tissue;

said blade having first and second opposed cutting edges;

said first edge lying substantially parallel to the long axis of said blade;

said second edge having a portion converging toward said first edge at an angle of from about 10 to 30 degrees;

the intersection of said edges including a transverse flat tip between said edges, said tip having a width of from about 0.50 to 0.30 mm and an angle to said first edge of from about 60° to 12020 ; and said edges and tip being faceted to provide sharp cutting edges.

9. The ophthalmologic surgical blade according to claim 8 wherein said angle of said flat tip to said first edge is from about 75° to 105°.

10. The ophthalmologic surgical blade according to claim 8 wherein said second edge lies at an angle to said first edge of about 15°.

11. The ophthalmologic surgical blade according to claim 8 wherein said tip has a width of approximately 0.20 mm.

12. The ophthalmologic surgical blade according to claim 8 wherein said blade thickness tapers over a portion near said tip.

13. The ophthalmologic surgical blade according to claim 8 wherein said blade length is about 1.4 mm, width is about 1.0 mm at said primal end, and thickness is about 0.15 mm at the primal end, with the blade thickness tapering over the last 1.5 mm adjacent to said tip at an angle of about 6° to each blade surface.

* * * * *